United States Patent [19]

Stadler et al.

[11] Patent Number: 4,613,714
[45] Date of Patent: Sep. 23, 1986

[54] CATALYST AND PROCESS FOR THE SELECTIVE HYDROGENATION OF MULTI-UNSATURATED ORGANIC COMPOUNDS

[75] Inventors: Karl-Heinz Stadler, Augsburg; Karel Kochloefl, Moosburg, both of Fed. Rep. of Germany

[73] Assignee: Süd-Chemie Aktiengesellschaft, Munich, Fed. Rep. of Germany

[21] Appl. No.: 785,472

[22] Filed: Oct. 8, 1985

Related U.S. Application Data

[62] Division of Ser. No. 614,638, May 28, 1984, abandoned.

[30] Foreign Application Priority Data

Jun. 6, 1983 [DE] Fed. Rep. of Germany ....... 3320388

[51] Int. Cl.⁴ .............................................. C07C 5/05
[52] U.S. Cl. .................................... 585/271; 585/259; 585/275
[58] Field of Search ......................... 585/271, 275, 259

[56] References Cited

U.S. PATENT DOCUMENTS

| | | | |
|---|---|---|---|
| 4,149,998 | 4/1979 | Tauster et al. | 502/325 |
| 4,171,320 | 10/1979 | Vannice et al. | 260/449 R |
| 4,292,203 | 9/1981 | Milberger et al. | |
| 4,457,823 | 7/1984 | La Conti et al. | 204/282 |

Primary Examiner—Curtis R. Davis
Attorney, Agent, or Firm—William R. Price

[57] ABSTRACT

Catalyst for the selective hydrogenation of multi-unsaturated organic compounds, in particular of diolefins and dienes in mixtures with other hydrocarbons; the catalyst is characterized by (A) a metal component from one or more elements of Group VIII of the Periodic Table on
(B) a support material on the basis
  (b$_1$) of one or more n-semiconducting oxides of one or more elements from the Subgroups IVb, Vb and VIb of the Periodic Table or of thorium or cerium, or respectively on the basis
  (b$_2$) of one or more n-semiconducting mixed oxide systems of the formula Me$_2$Me$_1$(O)$_x$, where Me$_1$ is an element of the group defined in (b$_1$), Me$_2$ an alkaline earth metal or an element different from Me$_1$ or the group defined in (b$_1$), and x signifies the number of oxygen atoms required for the saturation of Me$_1$ and Me$_2$ to the range of an n-semiconducting state;

the hydrogen chemisorption capacity, expressed as the atomic ratio between chemisorbed hydrogen atoms and metal atoms of the metal component (A) present on the surface of the metal particles, (H/Me$_A$), being at least 0.6:1.

10 Claims, No Drawings

CATALYST AND PROCESS FOR THE SELECTIVE HYDROGENATION OF MULTI-UNSATURATED ORGANIC COMPOUNDS

This is a division of application Ser. No. 614,638 filed May 28, 1984, and now abandoned.

FIELD OF THE INVENTION

The invention relates to catalysts and processes for the selective hydrogenation of multi-unsaturated organic compounds and in particular multi-unsaturated hydrocarbons.

BACKGROUND OF THE INVENTION

A number of selective hydrogenation reactions are of great technological interest. Olefin chemistry covers a broad field in petrochemistry. As an example, it is technologically important to remove diolefins from thermally cracked gasoline. The selective hydrogenation of butadiene is particularly noteworthy. Further, the selective hydrogention of isoprene or cyclopentadiene should be mentioned. It is very difficult to selectively hydrogenate dienes with isolated double bonds and in particular to control the hydrogenation of higher homologues of these dienes. They normally react during hydrogenation like mono-olefins, that is, they are immediately perhydrogenated to the corresponding alkane. If a selective hydrogenation is to be achieved which stops at the mono-olefin, the reaction should be preceded, according to the dogma, by a double bond isomerization to a conjugated diene. This isomerization is influenced, as a rule, by the surface property of the support material, for instance its acidity.

The most wide-spread and most economical catalyst systems for selective hydrogenation contain as catalytically active substances d-metals of Group VII of the Periodic Table on an inert oxide support material, in particular on aluminum oxide. Selectivity with respect to formation of alkenes from diolefins can be increased by a partial poisoning of the metal component, e.g., the palladium component, with Pb, Zn, Hg, Cd, Sn, etc. (so-called "Lindlar catalysts," cf. H. Lindlar, Helv. Chim. Acta, 35, 446 (1952) or generally G. C. Bond, "Catalysis by Metals," Academic Press, London, New York (1962), 99 and 297). On the other hand, correct dosage in the addition of the catalyst poison is a problem. Often the poisoned catalysts are either unselective or entirely inactive.

There exists further a number of commercial catalysts for selective hydrogenation. These catalysts contain palladium in concentrations of 0.03 to 0.5 wt.% on different aluminum oxides. Also a specific poisoning with Cr has been employed, about 0.5 wt.% Cr having been added. But these catalysts were often insufficiently selective or, if selective, insufficiently active.

SUMMARY OF THE INVENTION

It is the object of the invention to develop a supported catalyst which can be used for the selective hydrogenation of multi-unsaturated organic compounds, in particular of olefin-diolefin mixtures with a proportion of diolefins with isolated double bonds. Such a catalyst is characterized by
(A) a metal component from one or more elements of Group VIII of the Periodic Table on
(B) a support material on the basis ($b_1$) of one or more n-semiconducting oxides of one or more elements from the Subgroups IVb, Vb and VIb of the Periodic Table or of thorium or cerium, or respectively on the basis ($b_2$) of one or more n-semiconducting mixed oxide systems of the formula $Me_2Me_1(O)_x$, where $Me_1$ is an element from the group defined in ($b_1$), $Me_2$, an alkaline earth metal or an element different from $Me_1$ from the group defined in ($b_1$), and x signifies the number of oxygen atoms required for the saturation of $Me_1$ and $Me_2$ to the range of an n-semiconducting state; and in which the hydrogen chemisorption capacity, expressed as the atomic ratio between chemisorbed hydrogen atoms and metal atoms of the metal component (A) present on the surface of the metal particles, ($H/Me_A$), is at least 0.6:1.

The Subgroups IVb, Vb and VIb of the Periodic Table are defined according to "Handbook of Chemistry and Physics," 58th edition, 1978/79.

DESCRIPTION OF THE PREFERRED EMBODIMENT

The hydrogen chemisorption capacity ($M/Me_A$) can be determined by a volumetric method by letting a certain volume of hydrogen act on the catalyst at room temperature and ascertaining the volume decrease. Then the physically sorbed hydrogen is pumped off. The remaining portion, referred to the surface atoms of the metal component (A) accessible to hydrogen adsorption (atomic ratio), corresponds to the hydrogen chemisorption capacity of the catalyst. The catalyst according to the invention is characterized in particular by a hydrogen chemisorption capacity ($H/Me_A$) of 0.75 to 1:1.

It is essential that the n-semiconducting support material as herein defined is not to be regarded as chemically inert. In fact, a metal-support interaction develops during production or during use.

It is known that metal-support interactions substantially influence the adsorption properties of such a system. Thus, for example, German Patent Application DE-OS No. 27 13 457 describes catalyst mixtures with reduced hydrogen chemisorption capacity from a catalytic metal component, consisting of a metal of Group VIII of the Periodic Table on an oxide of the following transitional metals niobium, tantalum, vanadium, titanium, zirconium, hafnium or mixtures thereof. But also, alkaline earth titanates are described as support materials.

These catalysts are termed catalysts with "strong interactions between metal and support" (strong metal support interaction catalysts, abbreviated SMSI catalysts). The SMSI effect is obtained by an intensive reduction treatment of the catalyst precursor with hydrogen at temperatures between 475 and 775 K. The catalysts thus obtained have the special feature of a greatly reduced hydrogen chemisorption capacity ($H/Me_A$), which is at most about 2% of the initial value. As a result of this greatly reduced chemisorption capacity for hydrogen, these catalysts show an altered activity and selectivity behavior with respect to the dehydrocyclization of n-heptane or to ethane hydrogenolysis. In additional studies, it was found that $Ni/TiO_2$ catalysts which had been produced analogously to the process described in DE-OS No. 27 13 457 have a high activity and selectivity in the formation of methanol from CO (M. A. Vannice and R. L. Garten, J. Catal. 56, 236 (1979)). These catalysts, however, are not suitable for selective hydrogenation of multi-unsaturated organic compounds.

It has now been found, surprisingly, that the catalysts according to the invention, which differ from the mentioned catalysts mainly by the fact that their hydrogen chemisorption capacity (H/Me$_A$) is at least 0.6:1, are very suitable for the selective hydrogenation of multi-unsaturated organic compounds. With the catalysts of the invention, metal-support interactions do occur, due to the fact that the support material is an n-semiconductor, but they should not be understood as SMSI effects as taught by DE-OS No. 27 13 457. Probably the catalysts according to the invention involve metal-support systems were through adjustment of the Fermi level a "charge-transfer" interaction occurs (cf. C.-M. Schwab, Elektronik der Trägerkatalysatoren, Catalysis 25, 106 (1972)), which quantitatively and qualitatively influences the adsorption and also determines the chemical and physical properties of the adsorbate occurring in the catalytic process. Such an interaction should, in the case of TiO$_2$, in particular with simultaneous hydrogen adsorption, lead to the formation of Ti$^{3+}$-like "surface sites" which in turn can exert a selectively-promoting influence, for instance in that they act as dienophile coordination centers.

The catalyst according to the invention is characterized in particular by the fact that its metal component (A) is a noble metal from Group VIII of the Periodic Table, in particular palladium, and its n-semiconducting support material (B) represents either (b$_1$) an oxide of one of the elements from the Subgroups IVb, Vb and VIb of the Periodic Table, in particular Ti, Zr, V, Nb, Ta, Cr, Mo or W, or of thorium; or (b$_2$) SrTiO$_3$, BaTiO$_4$ or TiNb$_2$O$_7$.

In this connection the system Pd/TiO$_2$ is preferred.

Further the catalyst may contain, besides the n-semiconducting support material, an inert, non-n-semiconducting filling material, preferably aluminum oxide or silicon dioxide, magnesium oxide, calcium carbonate or the like. With the aid of the inert filling material the forming characteristics of the catalyst are improved. This is important because a catalyst in powder form has an increased flow resistance in the reactor and gives rise to increased dust formation. Also the diffusion behavior of the substances reacting at the catalyst is improved by the properties of the inert filling material. Lastly, the inert filling material brings about a dilution effect, whereby any exothermic temperature peaks are diminished. It suffices to make sure by appropriate process conditions that the metal component is adsorbed only at the n-semiconducting support materials, and not at the inert filling materials, so that a weak interaction between the metal component and the n-semiconducting support material occurs.

To obtain the only slightly reduced hydrogen chemisorption capacity, considered essential, the catalysts according to the invention can in principle be produced by two process variants.

According to the first process variant, the procedure generally is that a reducible compound of the metal component (A), e.g. a solution of a noble metal salt, is applied on a precursor of the n-semiconducting support material (B) and, under conditions in which the hydrogen chemisorption capacity (H/Me$_A$) of the obtained catalyst is maintained at at least 0.6:1, is reduced to the metal component (A).

This reaction is carried out preferably in a reducing atmosphere at temperatures at which the hydrogen chemisorption capacity (H/Me$_A$) does not drop below 0.6:1. These temperatures depend on the metal component/support material system used, on the reducing agent, and on time. For example, the reduction with hydrogen is carried out in a system-dependent manner below the following maximum temperatures in the course of 3 hours:

| System | Temp (K.) |
|---|---|
| Pd/TiO$_2$ | 470 |
| Pd/SrTiO$_3$ | 800 |
| Pd/BaTiO$_3$ | 800 |
| Pd/ZrTiO$_4$ | 500 |
| Pd/TiNb$_2$O$_7$ | 470 |
| Pd/CeO$_2$ | 600 |

Compared with the conditions stated in the DE-OS No. 27 13 457, therefore, the reduction is carried out under relatively mild conditions.

Alternatively, the reduction of the reducible compound of the metal component (A) can be carried out with a reducing agent such as formaldehyde or sodium formate, in liquid phase, preferably in aqueous medium. This is an especially mild form of the reduction treatment.

Alternatively, the reduction of the reducible compound of the metal component (A) can be carried out photochemically at ambient temperature, this being another mild form of the reduction treatment (cf. Dissertation, Karl-Heinz Stadler, Univeristy of Munich, 1982).

According to the other general process variant, the catalyst of the invention can be produced by applying a reducible compound of the metal component (A) on a precursor of the n-semiconducting support material (B), reducing it to the metal component (A) under conditions in which the hydrogen chemisorption capacity of the obtained catalyst (H/Me$_A$) drops below 0.6:1, and oxidizing the obtained catalyst until the hydrogen chemisorption capacity (H/Me$_A$) has again reached or exceeded the value of 0.6:1. This variant has the advantage that no special precautionary measures (observance of certain reduction temperatures and times) need to be taken in the reduction.

By the oxidation treatment, the catalyst, which by the reduction had been brought into the SMSI state undesirable for the present purpose under harsh conditions, is brought into a state desirable for selective hydrogenation of organic compounds in which there exists only a weak interaction between the metal component and the support material.

If for the above stated reasons a non-n-semiconducting filling material is to be added, it is added to the reduced catalyst, to make sure that the reduced metal component is not adsorbed at the inert filling material. That is, the reduced catalyst is mixed for example with aluminum oxide. In case of an additional thermal treatment, the formation of mixed oxide systems with aluminum oxide or the formation of oxides doped with Al$^{3+}$ should be precluded, since in this manner the n-semiconductor character of the support materials would be weakened.

If an inert filling material is added, the previous reduction treatment is carried out preferably according to the second process variant, that is, reduction under harsher conditions in order that the metal component will be bound more strongly to the n-semiconducting support material and will not migrate onto the inert support material. During the subsequent oxidation treatment for restoring the hydrogen sorption capacity, a migration of the metal component need no longer be feared.

As metal component (A) there is used preferably a noble metal whose content is between about 0.01 and 5%, by weight of the finished catalyst.

If aluminum oxide is used as inert filling material, a part thereof may be added in the form of aluminum stearate, for better forming characteristics (tablets, extrusions, etc.). Also, the titanium dioxide component may in part be added in the form of titanium stearate. During the oxidation treatment, these compounds are converted to the corresponding oxides.

The oxidation treatment may take place at temperatures to about 775 K., in particular for catalysts with titanium dioxide as support material.

The oxidation treatment may be followed by another reduction treatment, which however, should be conducted so that a transformation of the catalyst into the SMSI state is avoided.

Another possibility for the production of the catalysts of the invention, explained in the example of a $TiO_2$ catalyst, consists in precipitating a titanium oxide hydrate onto an inert, performed pulverized or granulated support material. This can be done, for example, by hydrolysis of $TiCl_4$, $TiOSO_4$, Ti-isopropylate; $TiCl_3$ or of other hydrolyzable titanium compounds. Also, the treatment of a preformed support material, for instance spherical $Al_2O_3$ of sufficiently high macroporosity, with a titanium dioxide sol, prepared by hydrolysis, for instance of Ti-isopropylate, leads to the precursor of the catalysts of the invention. Titanium oxide-containing supports, which are produced, for example, according to DE-PS No. 26 58 569 or according to DE-OS No. 24 46 496, are also suitable. A subsequent calcining step under an oxidizing atmosphere leads to the desired support materials. The application of the metal components, preferably noble metal components, takes place in the manner described before.

Lastly, it may prove to be advantageous for the improvement of the selectivity to impregnate the catalyst with phosphate- or fluoride-containing solutions. For this purpose, for example, a $H_3PO_4$ solution or a NaF solution is used. Preferably, this treatment is carried out with $TiO_2$ catalysts. The specific phosphate adsorption to the $TiO_2$ causes an increase of the surface acidity.

The area of use of the catalysts according to the invention is, as has been said before, the selective hydrogenation of multi-unsaturated organic compounds, in particular hydrocarbons. The catalysts of the invention are especially suitable for the selective hydrogenation of diolefins with isolated double bonds or respectively of dienes with cumulated and/or conjugated double bonds. The selective hydrogenation of the diolefins or dienes may be carried out in hydrocarbon mixtures containing said diolefins and dienes, including alkene-containing mixtures. It should be stressed that the hydrogenation of the diolefins to the corresponding alkenes can be carried out with high yields if the charge material contains non-conjugated diolefins with isolated double bonds with chain lengths of 10 to 15 or more carbon atoms.

Furthermore, the catalysts of the invention can be used also for the selective hydrogenation of unsaturated organic compounds which contain besides the $C=C$ double bond also $C=O$ and $C=N$ groups. Examples of these compounds are unsaturated esters, aldehydes, acid anhydrides and nitriles, such as acrolein, acrylic and methacrylic acid esters and nitriles, as well as maleic acid anhydride.

Another advantage consists in that the catalysts of the invention with a comparable noble metal content, or respectively a noble metal content lower by as much as 50%, reach higher or at least equal activities and above all higher selectivities than comparable catalysts with inert support materials.

The following Examples 1 to 10 will explain the production of some catalysts of the invention. In the comparison examples 1 to 3, the production of some known catalysts is indicated. Some physical and chemical data of the catalysts of the invention and of the comparison catalysts, including some commercial catalysts, are given in Table I. Tables II and III contain data which permit evaluating the superiority of the catalysts of the invention over the comparison catalysts. For this purpose, the selective hydrogenation of the diene component in mixtures of 1-hexene with 1,5-hexadiene were used. Additionally, the selective hydrogenation of the diene and diolefin component (about 10%) in corresponding $C_{10}$ mixtures was tested.

EXAMPLE 1

Titanium dioxide (spec. surface=50 m$^2$/8, 70% anatase, 30% rutile) is impregnated with an aqueous $PdCl_2$ solution to a Pd content of 0.5 wt.% and reduced in streaming $H_2$ for 3 hours at 675–725 K. This reduction step is omitted or is carried out at lower temperatures (below 470 K.) if a subsequent calcination in an oxidizing atmosphere is not performed. The catalyst can be used in the powder form obtained.

For dilution, the catalyst is thoroughly mixed with AlO(OH) as filling material (spec. surface=300 m$^2$/8, pore volume=0.46 ml/g) in the weight ratio 1:1, whereupon 3 to 4 wt.% Al stearate or Ti stearate are added, to facilitate shaping. After the material has been pelletized (4.5×4.5 mm), it is calcined for about 3 hours up to 775 K. with access of air. The Pd content now is 0.25 wt.%.

For the performing of the tests, the results of which are reported in Table II, the pellets were triturated once more, i.e., the catalyst was used as powder.

EXAMPLE 2

Titanium dioxide (spec. surface=50 m$^2$/g, 70 wt.% anatase, 30 wt.% rutile) is impregnated with $Sr(NO_3)_2$ or $Sr(OH)_2$, so that a product with a content of 10 wt.% SrO is obtained. This product is impregnated with aqueous $PdCl_2$ solution and reduced at 675–725 K. in streaming hydrogen. Thereafter, a procedure analogous to Example 1 is followed. The catalyst contains $SrTiO_3$ in accordance with the Sr quantity charged. Its Pd content is 0.25 wt.%.

EXAMPLE 3

The procedure of Example 1 is repeated, with the difference that a titanium oxide hydrate with a specific surface of 200 m$^2$/g is used.

EXAMPLE 4

The procedure of Example 1 is repeated with the difference that as support material a cerium dioxide with a specific surface of 60 m²/g is used and the reduction is carried out at 600 K.

EXAMPLE 5

The procedure of Example 1 is repeated with the difference that as support mateial a niobium pentoxide with a specific surface of 117 m²/g is used and the reduction is carried out at 670 K. This is followed by calcining with access of air.

EXAMPLE 6 p TiO₂ (50 m²/g) is impregnated with a PdCl₂ solution (0.25 wt.%). The product obtained is reduced with H₂ for 3 hours at 700 K. and subsequently impregnated with 0.3 m H₃PO₄ solution. The phosphate content is 0.5 to 2 wt.%. The impregnated product is calcined with access of air as stated in Example 1.

EXAMPLE 7

The procedure of Example 6 is repeated with the difference that the catalyst is impregnated with 0.3 m NaF solution. Thereafter the sodium ions are largely washed out with water. The fluoride content is 0.1 to 2 wt.%.

EXAMPLE 8

The procedure of Example 1 is repeated with the difference that besides aluminum oxide also 1 wt.% WO₃ is added to the product before pelletizing.

stearate, shaped to tablet size 4.5×4.5 mm. The tablets were impregnated with aqueous PdCl₂ solution, so that after the reduction (3 hours at 700 K.) a Pd content of 0.3 wt.% was obtained. The catalyst is calcined with access of air for 3 hours up to 775 K.

COMPARISON EXAMPLE 2

The procedure of Comparison Example 1 was repeated with the difference that instead of SiO₂ 5 wt.% of a HY molecular sieve were added.

COMPARISON EXAMPLE 3

A SiO₂ co-gel, in which 0.3 wt.% of the Si are replaced by Ti⁴⁺ (not in the form of titanium dioxide) (spec. surface 300 m²/g) is impregnated with an aqueous PdCl₂ solution, the Pd content being 0.25% after the reduction (3 hours at 700 K.). The catalyst is shaped to tablets of the dimensions 4.5×4.5 mm.

The catalysts were tested for their hydrogenating activity and selectivity. The results are given in Tables II and III.

When catalysts in powder form were used, the hydrogenation reaction was carried out in liquid phase in a 300-ml autoclave. 500 mg catalyst and 100 ml of a charge mixture of 1-hexene and 1,5 hexadiene (weight ratio 10:1) were used. The speed of agitation during the reaction was 1,000 rpm. The pressure was 5 bar; the temperature 348 K.

TABLE I

Physical and Chemical Data of the Catalysts Used

| Catalyst | | Dimensions (mm) | BET Surface (m²/g) | Bulk Weight (g/ltr) | Pore Volume (ml/g) | Pd (wt. %) |
|---|---|---|---|---|---|---|
| Example 1 | | 4.5 × 4.5 | 120 ± 10 | 870 ± 50 | 0.3 ± 0.05 | 0.20 ± 0.05 |
| 2 | | 4.5 × 4.5 | 110 ± 10 | 900 ± 50 | 0.2 ± 0.05 | 0.20 ± 0.05 |
| 3 | | 4.5 × 4.5 | 150 ± 10 | — | 0.2 ± 0.05 | 0.25 ± 0.05 |
| Example 4 | | 4.5 × 4.5 | — | — | — | 0.10 ± 0.05 |
| 5 | | 4.5 × 4.5 | — | — | — | 0.30 ± 0.05 |
| Example 6 | | 4.5 × 4.5 | 120 ± 10 | 870 ± 50 | 0.2 ± 0.05 | 0.20 ± 0.05 |
| 7 | | 4.5 × 4.5 | 120 ± 10 | 870 ± 50 | 0.2 ± 0.05 | 0.20 ± 0.05 |
| 8 | | 4.5 × 4.5 | 100 ± 10 | 900 ± 50 | 0.2 ± 0.05 | 0.20 ± 0.05 |
| Example 9 | | Powder | 50 | — | 0.0 | 0.50 |
| 10 | | Powder | 50 | — | 0.0 | 1.19 |
| Comp. 1 | | 4.5 × 4.5 | — | — | — | 0.30 ± 0.05 |
| ex. 2 | | 4.5 × 4.5 | — | — | — | 0.30 ± 0.05 |
| 3 | | 4.5 × 4.5 | 300 ± 20 | — | — | 0.25 ± 0.05 |
| (A) gamma Al₂O₃ + | 0.5% PD / 0.5% Cr | 4.5 × 4.5 T | 180 ± 10 | 900 ± 50 | 0.17 ± 0.05 | 0.5 ± 0.05 |
| (B) gamma Al₂O₃ + | 0.3% PD | 3–5 S | 95 ± 5 | 650 ± 50 | 0.57 ± 0.05 | 0.3 ± 0.05 |
| (C) gamma Al₂O₃ + | 0.3% PD | 4.5 × 4.5 T | 190 ± 10 | 850 ± 50 | 0.14 ± 0.05 | 0.3 ± 0.05 |
| (D) gamma Al₂O₃ + | 0.5 PD | 4.5 × 4.5 T | 185 ± 10 | 650 ± 50 | 0.14 ± 0.05 | 0.5 ± 0.05 |

(S = Spheres, T = Tablets, A-D Commercial Catalysts)

EXAMPLES 9 AND 10

Two g TiO₂ with a specific surface of 50 m²/g are suspended in 500 ml of an alcohol, e.g., ethanol; then enough aqueous PdCl₂ solution is added to give a Pd content, referred to 1 g TiO₂, of 0.56 or respectively 1.19 wt.%. For the reduction of the metal component the suspension is radiated with UV light under inert gas. The catalysts thus obtained are filtered and dried.

Besides the commercial catalysts used for comparison purposes, also some Pd-containing catalysts on non-n-semiconducting support materials were used, also for comparison purposes, the production of which is indicated in the following comparison Examples 1 to 3.

COMPARISON EXAMPLE 1

Hydrated aluminum oxide (AlO(OH) (spec. surface=300 m²/g; pore volume=0.46 ml/g) was mixed with 5 wt.% SiO₂ and, after addition of 3 wt.% Al

TABLE II

Hydrogenation of a Mixture of 1-Hexene and 1,5-Hexadiene

| Catalyst | t₁ (min) | t₂/t₁ | S_½ |
|---|---|---|---|
| Example 1 | 20 | 25 | 100 |
| Example 2 | 22 | 27 | 100 |
| Example 3 | 16 | 11 | 100 |
| Example 4 | 11 | 14 | 100 |
| Example 5 | 5 | 14 | 100 |
| Example 6 | 30 | 12 | 100 |
| Example 7 | 35 | 14 | 100 |
| Example 8 | 18 | 11 | 100 |
| Example 9 | 30 | 12 | 100 |
| Example 10 | 30 | 11.7 | 100 |
| Comp. ex. 1 | 15 | 11 | 93 |
| Comp. ex. 2 | 10 | 9 | 92 |
| Comp. | 93 | 2 | 40 |

TABLE II-continued

Hydrogenation of a Mixture of 1-Hexene and 1,5-Hexadiene

| Catalyst | $t_1$ (min) | $t_2/t_1$ | $S_{\frac{1}{2}}$ |
|---|---|---|---|
| ex. 3 | | | |
| Cat. A | 35 | 4.6 | 76 |
| Cat. B | 95 | 1.9 | 88 |

REMARKS selectivity S is defined by the percentual proportion of hexane, formed from 1,5-hexadiene, in the formed total hexane quantity at time $t_1 = \frac{1}{2}$.

$t_1$ is the time in min. to complete 1,5-hexadiene hydrogenation.

$t_2$ is the time in min. to complete hexene hydrogenation.

The greater the $t_1/t_2$ ratio, the more advantageous is the hydrogenation activity of the catalyst in the 1,5-hexadiene hydrogenation.

Tablet shaped catalysts (dimensions 4.5 × 4.5 mm) were used for the hydrogenation of 1-decene/1,9-decadiene mixtures. The hydrocarbon mixtures were prepared from the commercial components. The diene content was in each instance about 6 wt. %. A 1-liter autoclave was used. The charged quantity was 300 ml. There were 10 g catalysts in a basket which moved up and down during the reaction between liquid phase and gas phase. Thereby, a so-calld "trickle phase" hydrogenation was simulated. The pressure in the individual tests was 5, 10 and 30 bar; the temperature 348 and 378 K.

TABLE III

Hydrogenation of a $C_{10}$-Olefin-Diolefin Mixture

| Catalyst | $t_{1/5}$ (min) | $S_{1/5}$ | $S^+$ | P (bar)/T (K) |
|---|---|---|---|---|
| Example 1 | 39 | 38 | 30 | 20/348 |
|  | 51 | 100 | 78 | 5/373 |
| Example 2 | 37 | 100 | 53 | 20/348 |
|  | 43 | 100 | 75 | 10/348 |
| Example 8 | 54 | 100 | 41 | 20/348 |
| Cat. A | 88 | 10 | 38 | 20/348 |
| Cat. B | 22 | 12 | 13 | 20/348 |
| Cat. C | 37 | 7 | 0 | 30/348 |
| Cat. D | 53 | 14 | 47 | 20/348 |

REMARKS $t_{1/5}$ is the time that was needed to reduce the original diolefin portion (10 wt. %) to 1/5 (2/5).

$S_{1/5}$ is the ratio of the percentual diolefin conversion to the olefin conversion at time $t_{1/5}$. S > 100 means that also a part of the existing olefin is hydrogenated to alkane, not only the diolefin.

$S^+$ indicates what percentual proportion of the consumed diolefin is transformed into olefin (after a reaction time of 10 min).

We claim:

1. Process for the selective hydrogenation of highly-unsaturated organic compounds in a mixture of hydrocarbons, which comprises the steps of:
   A. contacting said mixture of hydrocarbons with hydrogen in the presence of a catalyst comprising:
   B. a metal component of an element of Group VIII of the Periodic Table on
   C. a support material, selected from the group consisting of:
      ($c_1$) one or more n-semiconducting oxides of one or more elements from Subgroups IVb, Vb and VIb of the Periodic Table or of thorium or cerium, and
   D. in which the hydrogen chemisorption capacity, expressed as the atomic ratio between chemisorbed hydrogen atoms and metal atoms of the metal component (A), present on the surface of the metal particles, ($H/Me_A$) is at least 0.6:1.

2. Process, as defined in claim 1, in which said highly-unsaturated organic compounds contain multi-unsaturated chemical bonds.

3. Process, as defined in claim 1, in which said highly-unsaturated organic compounds are hydrocarbons.

4. Process, as defined in claim 1, in which said highly-unsaturated organic compounds are diolefins with isolated double bonds.

5. Process, as defined in claim 1, in which said highly-unsaturated organic compounds are dienes with cumulated double bonds.

6. Process, as defined in claim 1, in which said highly-unsaturated organic compounds are dienes with conjugated double bonds.

7. Process, as defined in claim 1, in which said highly-unsaturated organic compounds comprise diolefins in a mixture of hydrocarbons containing mono-olefins.

8. Process, as defined in claim 1, in which said mixture of hydrocarbons is contacted with hydrogen in the liquid phase.

9. Process, as defined in claim 1, in which said mixture of hydrocarbons is contacted with hydrogen in the gaseous and liquid phase.

10. Process, as defined in claim 1, in which the n-semiconducting oxide of the support material C is in the form of an n-semiconducting mixed oxide system, corresponding to the formula $Me_2Me_1(O)_x$, where $Me_1$ is an element in the group defined in ($c_1$), $Me_2$, an alkaline earth metal or an element different from $Me_1$ of the group defined in ($c_1$) and x signifies the number of oxygen atoms required for the saturation of $Me_1$ and $Me_2$ to the range of an n-semiconducting state.

* * * * *